United States Patent [19]

Conte et al.

[11] Patent Number: 5,594,030
[45] Date of Patent: Jan. 14, 1997

[54] CONTROLLED RELEASE PHARMACEUTICAL COMPOSITIONS BASED ON ONE OR MORE PHARMACEUTICALLY ACCEPTABLE SALTS OF GAMMA HYDROXY-BUTYRIC ACID

[75] Inventors: Ubaldo Conte, Busto Arsizio; Aldo La Manna, Pavia; Giuseppe Tessitore, Sanremo, all of Italy

[73] Assignee: Laboratorio Farmaceutico C.T. S.r.l., Sanremo, Italy

[21] Appl. No.: 278,517

[22] Filed: Jul. 21, 1994

[30] Foreign Application Priority Data

Jul. 22, 1993 [IT] Italy ................ MI93A1631

[51] Int. Cl.⁶ ........................................ A61K 31/185
[52] U.S. Cl. .................... 514/553; 424/461; 424/462; 424/469; 424/480; 514/811; 514/812; 514/813
[58] Field of Search ..................... 424/461, 462, 424/470, 469, 480; 514/553, 811, 812, 813

[56] References Cited

U.S. PATENT DOCUMENTS 4,983,632 1/1991 Gessa et al. .................. 514/557
5,316,772 5/1994 Jurgens, Jr. et al. ............ 424/462

FOREIGN PATENT DOCUMENTS

| 325086 | 7/1989 | European Pat. Off. . |
| 344704 | 12/1989 | European Pat. Off. . |
| 139519 | 1/1980 | Germany . |
| WO93/00083 | 1/1993 | WIPO . |

OTHER PUBLICATIONS

Database WPI; Week 7802, 15 Apr. 1977, Derwent Publication Ltd., London, GB; AN 78-03570A (Jan. 1972).
Goodman & Gilman, Pharmacological Basis of Therapeutics, (1985) MacMillan & Co. NY pp. 382-383.

*Primary Examiner*—Brian M. Burn

[57] ABSTRACT

Controlled release pharmaceutical compositions administrable by oral route, containing as the active principle at least one salt of the gamma hydroxy butyric acid with a pharmaceutically acceptable cation, for the treatment of alcoholism, opium like substances addiction, heroin addiction, food and nicotine addiction, depressive and anxious states, composed by:
a) a nucleus in the form of granules and tablets comprising an active principle dispersed in a particular cellulosic matrix; and optionally by:
b) a filming protection of the nucleus.

12 Claims, 5 Drawing Sheets

CONTROLLED RELEASE PHARMACEUTICAL COMPOSITIONS BASED ON ONE OR MORE PHARMACEUTICALLY ACCEPTABLE SALTS OF GAMMA HYDROXY-BUTYRIC ACID

FIELD OF THE INVENTION

The present invention relates to pharmaceutical compositions having a controlled release, administrable by oral route, containing as the active principle at least one salt of the gamma-hydroxy butyric acid with a pharmaceutically acceptable cation, said compositions being suitable in particular for the treatment of alcoholism, opium like substances addiction, heroin addiction, food and nicotine addiction, as well as in the treatment of depressive and anxious states.

PRIOR ART

In industrialized countries, alcohol has the peculiarity of being the only pharmacological agent susceptible of a socially accepted autointoxication, and excluding cigarette addiction, alcoholism is the most serious social problem in all the industrialized countries. If measured in terms of accidents, lose of productivity, crimes, death and diseases, the social cost of this problem is incalculable due to is the cost for ruined families, lost lives, loss for the society and human troubles.

The ethyl alcohol addiction starts when the alcohol consumption of the individual exceeds the limits accepted by its culture, damages its health or interferes with its social relations; alcohol addiction occurs at any level: at the lowest levels, alcohol is desired or is needed both as food and as social relationship means. At a medium level, alcohol addiction happens when an individual feels the necessity to drink in order to work or participate to social life and tries to increase the alcohol consumption to reach these aims. We observe a marked alcohol addiction when the individual drinks more alcohol than the usual social and cultural habits allow, drinks in situations in which he normally would not and he assumes alcohol even from toxic liquids that normally are not used as beverages.

If alcohol is continuously consumed, the individual needs a slight, but continuous increase in the threshold necessary to maintain a certain level of alcohol in the blood.

Moreover a physiological and psychological adaptation take place, and the alcoholic appears less poisoned and less affected in the "performance tests" at a certain concentration of alcohol in the blood, if compared to the same test carried out on unaddicted patients.

Physiological addiction to alcohol and the abstinence syndrome happen when the alcohol consumption is reduced below the critical level. The damage caused to the individual by alcohol addiction can be quantitatively higher than those caused by any other type of addiction.

Alcohol alters mental faculties and psychomotor coordination producing a reduction in the working capacity. Reduction in mental faculties cause mistakes in business, and damage social relations; the behaviouristic conscious controls are dissolved with consequent exhibitionism and aggressiveness, moreover alcohol addiction predisposes and causes serious physical disorders, also consequential, because of neglect in hygienic conditions or inadequate diet with deficiency in proteins and mineral salts.

The most serious complication in alcoholism is the cirrhosis.

The most largely used drug in chronic alcoholism therapy is Disulfiram (Antabuse); this therapy is based on the fact that a subject treated with Disulfiram shows unpleasant and clinically detectable symptoms when assuming alcohol.

Disulfiram by itself although not being completely innocuous is scarcely toxic when it is administered only at therapeutical doses. Nevertheless the same principle deeply alters metabolism of alcohol with the result that, when alcohol is administered to an animal or to an individual previously treated with Disulfiram, the blood acetaldehyde concentration rises five to ten times higher than in an animal of individual only treated with the same dose of alcohol.

This effect is accompanied by signs of symptoms known as the "acetaldehyde syndrome" or "Disulfiram alcohol reaction" and it is now generally accepted that most of these dramatic symptoms observed after ingestion of alcohol plus Disulfiram are attributable to the resulting increase in the concentration of acetaldehyde in the body, being these symptoms observable also after intravenous injection of acetaldehyde.

Patients treated with this substance refuse alcoholic beverages to avoid the unpleasant toxic and sometimes fatal effects due to acetaldehyde accumulation (Goodman & Gilman, The pharmacological basis of therapeutics, 7th edition, pages 382–383, 1985).

Finally, Disulfiram is not completely innocuous and may cause acneiform eruptions, allergic dermatitis, urticaria, lassitude, fatigue, tremor, restlessnes, reduced sexual potency, gastric or digestive disturbances and moreover being an aspecific enzymatic inhibitor, alters the activity of all enzymes having the —SH group, as the active site causing consequently more damage to the organism. Nevertheless these are mild effects if compared to the reaction that may result from the ingestion of very small amounts of alcohol in person treated with Disulfiram; as a consequence of Disulfiram treatment, depression, myocardial infarction, sudden and unexplained fatalities have occurred.

Obviously the use of Disulfiram as a therapeutic agent is not without danger, and should be attempted only under careful medical supervision.

As described in U.S. Pat. No. 4,983,632 in the name of the Assignee, 4-hydroxy butyric acid salts showed unexpected properties in reducing the desire and the addiction to alcohol in alcoholic patients.

As described in the U.S. patent application, in the name of the assignee Ser. No. 08/217,596 filed on Mar. 24, 1994 (now abandoned), sodium gamma hydroxy butyrate is used in the treatment of depressive and anxious states.

In the PCT Patent Application No. WO93/00083 of Jun. 23, 1992 the use is described of the same active principle in the treatment of the opium like substances addiction, heroin addiction, food and nicotine addiction.

However, sodium gamma hydroxy butyrate, shows an inconvenient since is absorbed quickly and shows a maximum peak about 30–45 minutes after the administration and has a half life of 20–25 minutes.

Besides, the elimination is quite quick; in fact this principle is eliminated in 4–5 hours. All these data, can be deduced from table 1 and FIG. 1 reported hereinbelow.

In view of the foregoing, the active ingredient has to be administered many times day, in particular, at least 4 times in order to assure a desirable pharmacological effect in patients showing a marked craving who need a continuous and constant therapy, especially in the first period of the treatment.

There is a need to have pharmaceutical compositions in solid form, for oral administration, which with respect to the presently used syrupy solution, show a suitably modulated release of the above mentioned principle.

SUMMARY OF THE INVENTION

The assignee has now unexpectedly found pharmaceutical compositions administrable by oral route, having controlled release containing one or more salts of the gamma hydroxy butyric acid with pharmaceutically acceptable cations which can overcome the above mentioned drawbacks.

In particular, the pharmaceutical compositions having controlled release according to the present invention, consist of:

a) a nucleus in the form of granules or tablets comprising an active principle dispersed in a cellulosic matrix consisting of a mixture of ethylcellulose and a cellulosic compound selected from methylcellulose, hydroxy-propyl-methyl-cellulose, hydroxy-propyl-cellulose.

and optionally by:

b) a film coating consisting of copolymers of acrylic and metacrylic acid esters in combination with lower alcohols of the same type, but substituted with quaternary alkylammonium groups, or a film protection of the nucleus from the external agents.

The compositions of the present invention are particularly suitable in the treatment of alcoholism, opium like substances addiction, heroin addiction, food and nicotine addiction, as well as in the treatment of depressive and anxious state.

BRIEF DESCRIPTION OF THE DRAWINGS

Internal diagram shows the relation between the area below (AUC) curve and the GHB dose. Dotted line shows the relation evaluated between the lower values of the data couple AUC-dose on the base of a linear kinetic;

FIG. 3 shows the release of the active ingredient in the composition of Example 2 (RET-4) containing respectively:

☐ 3.7% of filming coating

◇ 4.9% of filming coating

Δ 8.2% of filming coating as a function of the time;

FIG. 4 shows the gas chromatographic dosage in plasma, in mcg/ml, as a function of the time, of the following compositions:

☐ RET-5, the composition of Example 1

◇ RET-4, the composition of Example 2;

FIG. 5 shows the gas chromatographic dosage in plasma, in mcg/ml, as a function of the time, of:

☐ RET-5

◇ RET-4

Δ ALCOVER syrup

DETAILED DESCRIPTION OF THE PRESENT INVENTION

In the description reported hereinbelow, the following abbreviations are reported:

GHB=gamma hydroxy butyric acid NaGHB=sodium salt of gamma hydroxy butyric acid.

Gamma hydroxy butyric salts used in compositions having a controlled release according to the present invention are preferably selected from the group consisting of sodium, lithium, potassium, magnesium and calcium salts.

Particularly preferred pharmaceutical compositions according to the present invention are those wherein the nucleus (a) contains the dispersed active principle in the above mentioned cellulosic matrix resulting covered by the above mentioned filming coating (b).

The cellulosic matrix contained in the nucleus consists of ethylcellulose and a cellulosic compound selected from methylcellulose, hydroxy-propyl-methyl-cellulose, hydroxy-propyl-cellulose having different molecular weights and is present in an amount comprised between 2.5 and 75 % by weight based on the weight of the active principle and the weight ratio between ethyl cellulose and the above mentioned cellulosic compound is comprised between: 5 and 50%.

Hydroxy propyl methylcellulose having high molecular weight and high viscosity ranging preferably from 2,000 to 1,000,000 cps, is preferably used, at least 50% of the granulometry of this product has to be comprised between 20 and 200 microns, and preferably between 50 and 150 microns; the product with the trademark Methocel® K 100M, having a viscosity of 100,000 cps is preferably used.

The ethylcellulose preferably used has a viscosity comprised between 5 and 200 cps, and it is more preferably used ethyl cellulose with an average viscosity of 22 cps produced by BDH®.

In the compositions according to the present invention, these cellulosic polymers can be used as dry products, or a portion thereof can be used in solution or dispersion, preferably in an organic solvent or a non aqueous solvent in order to obtain a binding effect during the production process of the granulate.

The nucleus of the pharmaceutical compositions according to the present invention can optionally contain also other excipients selected from antisticking agents, agents able to give the correct degree of lubrication, moisture proof agents or mixtures thereof. Preferably in the compositions according to the present invention, talc is used as antisticking agent, magnesium stearate as lubricating and colloidal silica as moisture proof agent.

Nucleus (a) comprises the active principle dispersed in a cellulosic matrix as above defined, both in the form of granules or tablets and is able to transfer 40–50% of the active principle within the first hour and to free the remaining amount during the following 6–7 hours.

The pharmaceutical compositions according to the present invention contain preferably also a Filming coating, allowing to extend the above mentioned release time of the GHB salts.

The copolymers forming the filming coating show inside the polymeric chain the following repeating units.

wherein $R_1$ is H or methyl, $R_2$ is methyl or ethyl, $R_3$ is methyl, $R_4$ is $-CH_2CH_2N^{(+)}(CH_3)_3Cl^{(-)}$ Those copolymers are generally used whose content of the monomeric unit: ethyl trimethylamonium methacrylate chloride is comprised between 2 and 15% by weight, preferably between 5 and 10% by weight.

Tipically a mixture of copolymers containing 5% by weight of said monomeric unit (Eudragit® RS) and copolymers containing 10% by weight of the same monomeric unit (Eudragit® RL), these copolymers being present respectively in weight ratio comprised between 0.5:10 and 10: 0.5. The preferred weight ratio is 1:4.

The filming coating is preferably present in an amount comprised between 2.5 and 20% by weight on the total nucleus weight. By increasing (b) amount, the thickness increases of the resulting filming coating (b) present on the surface of the granules or of the tablets according to the present invention, thereby permitting to further extend the modulated release in time of GHB salts (see FIG. 3).

In place of the above mentioned filming coating having the purpose to further protract the active principle release, other filming types can be used having essentially a protective function of the nucleus from the external agents. These films consist of polymers such as hydpoxy propyl-cellulose, hydroxy-propyl-methylcellulose, polyvinyl-pyrrolidone, polyoxyethylen glycol.

The present invention further relates to the process for the preparation the above mentioned controlled release pharmaceutical compositions.

In particular it comprises the following steps:

i) the active principle is dry-mixed with the cellulosic product selected from methyl cellulose, hydroxy-propyl methyl cellulose hydroxypropyl cellulose and optionally a portion of ethylcellulose and the remaining part of ethylcellulose is added in the form of a solution, suspension or dispersion in an alcoholic solvent, preferably ethanol, the mixture is granulated under wet conditions, then the obtained granulate is dried thus obtaining controlled release pharmaceutical compositions in the form of granules wherein the nucleus (a) contains the active principle dispersed in the cellulosic matrix;

ii) the granulate from step (i), optionally added with excipients selected from antisticking agents, lubricating agents and moisture proof agents or mixtures thereof, is subjected to compression in order to obtain the corresponding tablets, thus obtaining the nucleus consisting of an active principle dispersed in the cellulosic matrix, in the form of tablets;

iii) the granulate from step (i) or the tablets from step (ii) are film coating by spraying a dispersion containing from 2 to 10% by weight of copolymers of acrylic acid or metacrylic acid esters with lower alcohols and with substituted alcohols with quaternary alkylamonium groups, in a mixture of one or more alcoholic solvents and/of one or more ketonic solvents; isopropanol and acetone are preferably used in a 1:1 volume ratio, said dispersion optionally containing one or more plasticizers, as for example diethylphthalate, dibutylphthalate, castor oil and polyethylenglycol in concentrations comprised between 0.5 and 20% by weight calculated on the dry copolymer weight or iii') the granulate obtained as described in step (i) or the tablets obtained as described in step (ii) are subjected to a filming protection.

Suitable copolymers of acrylic and metacrylic acid esters used in step iii) of the process according to the present invention are the above mentioned esters Eudragit® RS, EL or the corresponding mixtures.

The polymers used in step iii') are selected from hydroxypropyl-cellulose, hydroxy-propyl-methyl-cellulose, polyvinyl-pyrrolidone, polyoxyethylene glycol.

The granulate prepared in step (i) must have an appropriate and characteristic density to be suitable for compression.

In particular it was found that values of Hausner index (ratio between the final constant density and the density after 10 strokes in a suitable press) comprised between 1 and 1.5, and values comprised between 5 and 20 of Carr index (ratio between the difference of the above mentioned 2 densities and the final density expressed by percentage) are valid.

The following examples of delayed release compositions of the present invention and the relative preparation process are reported for illustrative but not limitative purpose.

EXAMPLE 1

| Tablet | |
|---|---|
| GHBNa | 1000 mg |
| Ethylcellulose BDH ® 22 Cps | 50 mg |
| Methocel ® K100M | 150 mg |
| Talc | 60 mg |
| Magnesium stearate | 18 mg |
| total | 1278 mg |
| Eudragit ® coating composition in 100 cc of solvents mixture | |
| Eudragit ® RS100 | 1.20 g |
| Eudragit ® RL100 | 4.80 g |
| Diethylphthalate | 0.30 g |
| Anhydrous acetone | 50 ml |
| Isopropyl alcohol | 50 ml |

Preparation

20 Kg GHBNa and 3.0 Kg Methocel® K100M are mixed in a suitable wet granulator.

After 15 minutes, 5 liters of a 20% suspension of ethylcellulose BDH® 22 Cps in ethyl alcohol are slowly added in about 10 minutes, then the uniformly wet mixture is forced onto a 16 mesh (810 microns) sieve and the obtained granulate is dried at 60° C. for about 2 hours.

The obtained product is mixed for about 20 minutes with 1.2 kg talc and 360 g magnesium stearate.

The obtained mixture can be directly used as such or can be compressed thus obtaining the final tablets containing 1.0 g GHBNa.

The film coating is prepared by dispersing 24.0 g Eudragit® RS, 96.0 g Eudragit® RL and 6.0 g diethylphthalate in 2000 ml acetone isopropyl alcohol 1:1 mixture.

The obtained solution or suspension is placed on the granules or on the tablets previously prepared by suitable spray guns, in order to obtain on every granule or tablet an amount of film coating comprised between 2.5 and 20% by weight on the nucleus weight.

EXAMPLE 2

| Tablet | |
|---|---|
| GHBNa | 1000 mg |
| Ethylcellulose BDH ® 22 Cps | 70 mg |
| Methocel ® K100M | 160 mg |
| Talc | 25 mg |
| Magnesium stearate | 15 mg |
| colloidal silica | 7 mg |
| total | 1277 mg |
| Eudragit ® coating composition in 100 cc of solvents mixture | |
| Eudragit ® RS100 | 1.20 g |
| Eudragit ® RL100 | 4.80 g |
| Diethylphthalate | 0.30 g |
| Anhydrous acetone | 50 ml |
| Isopropyl alcohol | 50 ml |

Preparation

20 Kg GHBNa and 3.2 Kg Methocel® K100M are mixed in a suitable wet granulator.

After 15 minutes, 7 liters of a 20% suspension of ethylcellulose BDH® in ethyl alcohol are slowly added in about 10 minutes, then the uniformly wet mixture is forced through a 16 mesh (810 microns) sieve and the obtained granulate is dried at 60° C. for about 2 hours.

The obtained product (about 24.6 kg) is mixed for about 20 minutes with 0.5 kg talc, 300 g magnesium stearate and 140 g colloidal silica.

The obtained mixture can be directly used as such or it can be compressed thus obtaining the final tablets containing 1.0 g GHBNa. The filming coating is prepared as described in the previous example.

EXPERIMENTAL TEST

In formulation represented by aqueous liquid solutions, such as those at the moment on the market, GHBNa is rapidly absorbed and during an in vitro tests for the evaluation of the dissolution during the time, an instantaneous release for 100% of the active substance is present.

Figures 1, 1A:
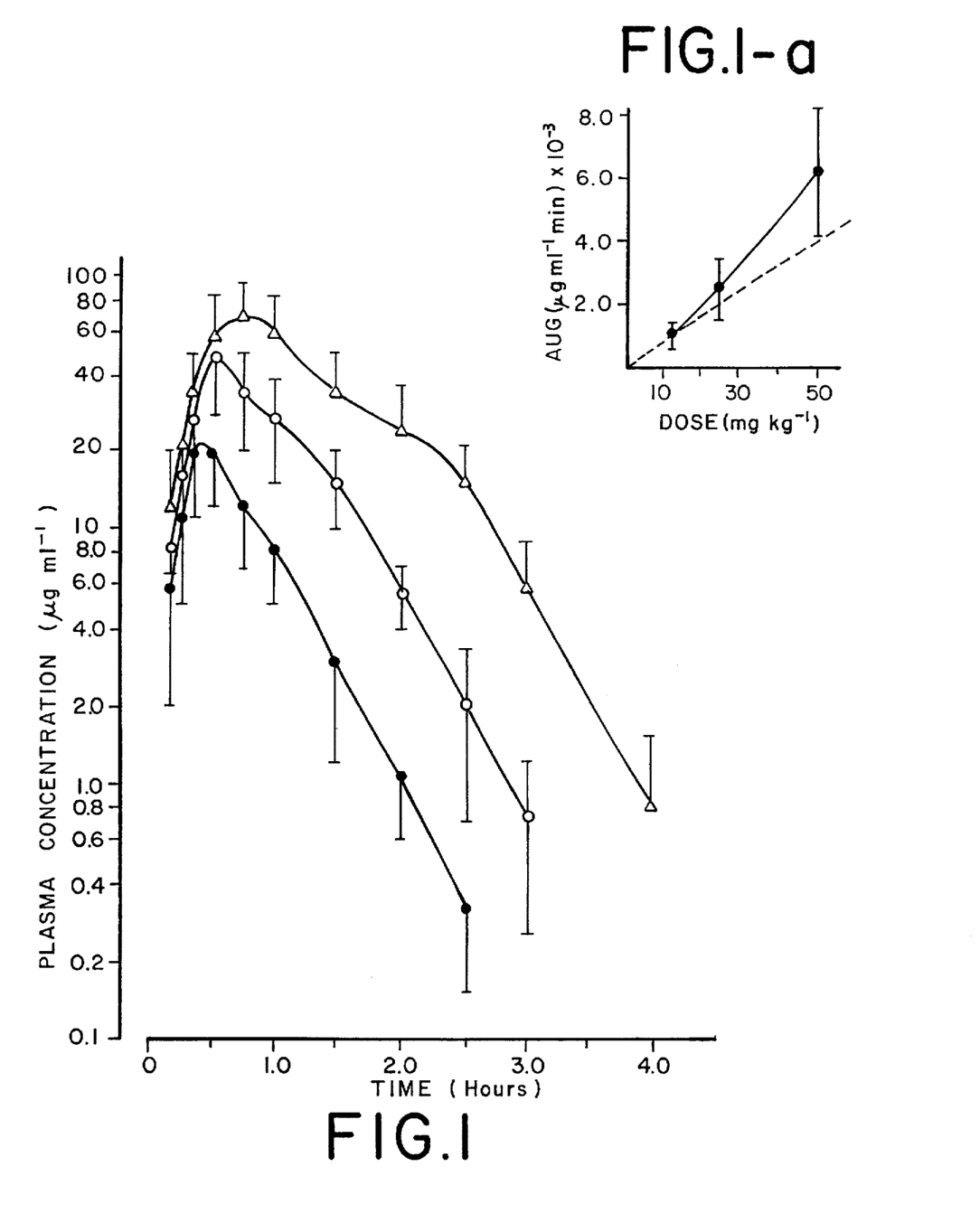
FIG. 1 shows a semilogarithmic diagram of the average concentrations (SD) in plasma after oral administration of 12.5 (●), 25 (o) and 50 (Δ) mg/kg of GHB.

In vivo, GHBNa is rapidly absorbed, and, if administered in formulation having an immediate release, shows the above mentioned results reported in FIG. 1 and table 1.

TABLE 1

GHB Average pharmacokinetic parameters after administration of different doses to 8 healthy volunteers

| Parameter | Dose (mg/kg) | | |
|---|---|---|---|
| | 12.5 | 25 | 50 |
| AUC (µg/ml min) | 905 (443) | 1271 (560)a | 1565 (548)a |
| $CL_o$ (ml min$^{-1}$kg$^{-1}$) | 14 (6) | 9 (4)* | 7 (3)** |
| MRT (min) | 45 (10) | 53 (9)** | 70 (12)** |
| $t^{1/2}$ z (min) | 20 (2) | 22 (3)** | 23 (3)* |
| $C_{max}$ (µg/ml) | 23 (9) | 23 (11)a | 20 (7)** |
| $t_{max}$ (min) | 25 (20–30)b | 30 (20–45)b* | 45 (30–60)b** |
| $f_u$ | 0.99 (0.03)c | | | anormalized at 12.5 mg/kg
baverage value (range)
cdetermined at a predialysis concentration of 25 µg/ml
*p < 0.05 and p < 0.01 related to values obtained with the group treated with 12.5 mg/kg dose, wherein AUC indicates the area under the curve, $CL_o$ the oral clearance, MRT the average residence time, $t^{1/2}$ z final halflife time, $C_{max}$ concentration corresponding to hematic peak, $t_{max}$ absorption time to the peak, $f_u$ fraction of unbound drug.

In a solid pharmaceutical form, with a gradual release in the time, the situation may drastically change already in vitro with a quite retarded release that, for the in vivo transposition may reduce substantially the global dosage and reduce the number of daily administration and therefore promote the adhesion of the patient to the pharmacological therapy.

The evaluation test in vitro is carried out with a dissolution test consistent with the apparatus described in the European Pharmacopoeia 2° ed. or UPS XXII ed. ("paddle test"). The dosage, evaluated in the time after 1, 2, 3, 4, 6 and 8 hours, is carried out with 1N hydrochloric acid, taking a known amount from the dissolution medium.

Operating Conditions:
medium: distilled H20 900 ml.
temperature: 37° C.
rpm: 110
titrating agent 1N HCl.

The retardant effect due to solid formulations reported in the examples is clear.

In the nucleus tablet, obtained with the process reported in example 2, without the coating, a retardant effect with prolonged release in the time is already obtained.

Data obtained are the following (expressed as GHBNa percentage with respect to the total tablet content):

TABLE 2

| 1st hour | 51.2% |
|---|---|
| 2nd hour | 69.1% |
| 3rd hour | 79.0% |
| 4th hour | 85.5% |
| 6th hour | 93.3% |
| 8th hour | 97.2% |

Figure 2:
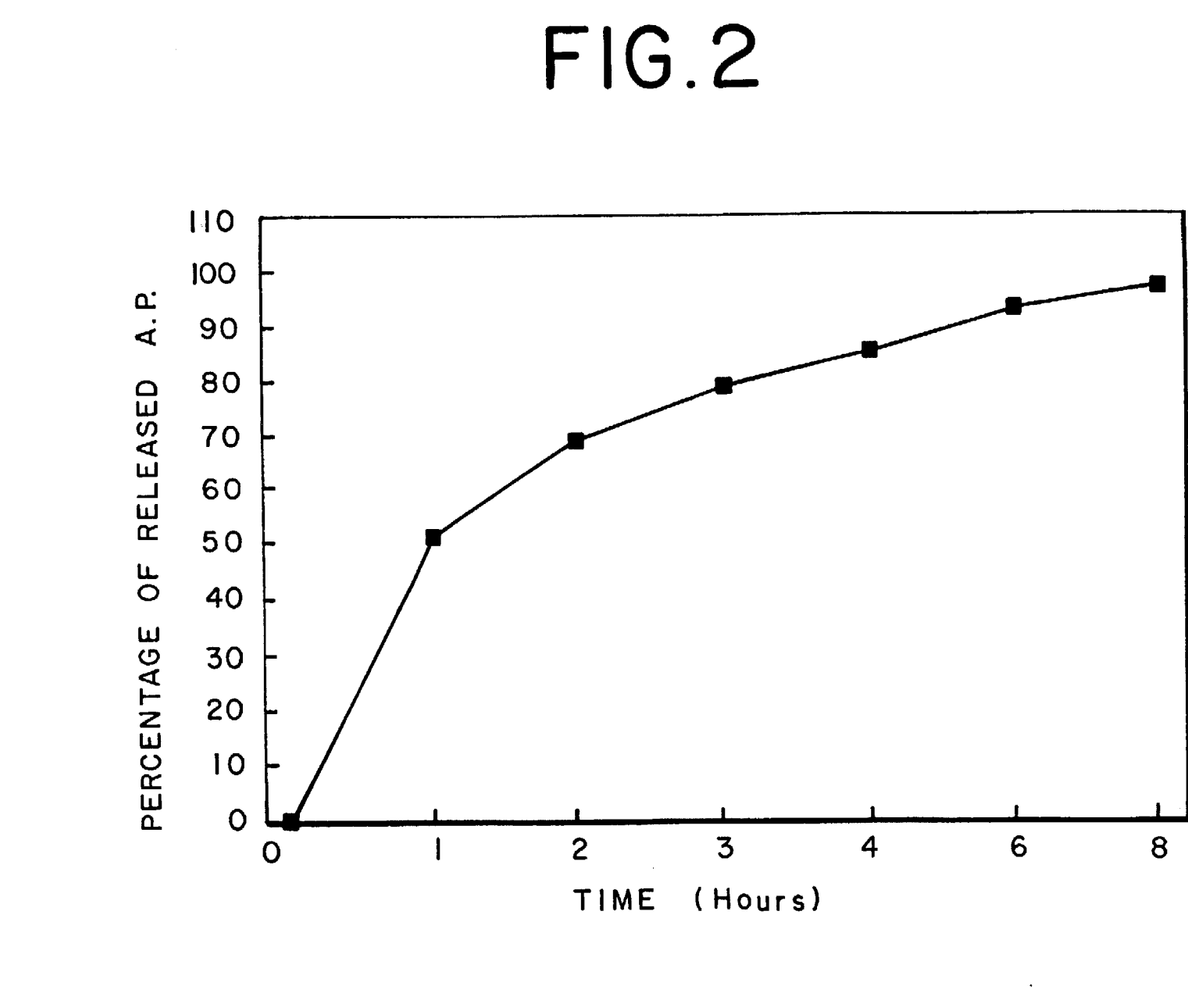
FIG. 2 shows the release of the active ingredient of the composition of Example 2 (RET-4) not containing the filming coating as a function of the time.

The corresponding dissolution profile is reported in FIG. 2.

Coupling these formulations with a filming and retardant coating based on Eudragit® mixtures, as described in the example above reported, GHBNa release in the time, can be further and remarkably extended.

The retardant effect is obviously a function of the amount of coating applied on the base nucleus.

Analytical data obtained for 3 different compositions corresponding to 3.7%, 4.5% and 8.2% of applied filming matrix are reported in table 3.

TABLE 3

| | 3.7% | 4.5% | 8.2% |
|---|---|---|---|
| 1st hour | 35.1 | 29.7 | 16.0 |
| 2nd hour | 57.4 | 52.9 | 38.3 |
| 3rd hour | 70.1 | 65.1 | 57.1 |
| 4th hour | 77.1 | 73.6 | 67.1 |
| 6th hour | 88.2 | 88.2 | 82.6 |
| 8th hour | 92.2 | 93.1 | 91.8 |

Figure 3:
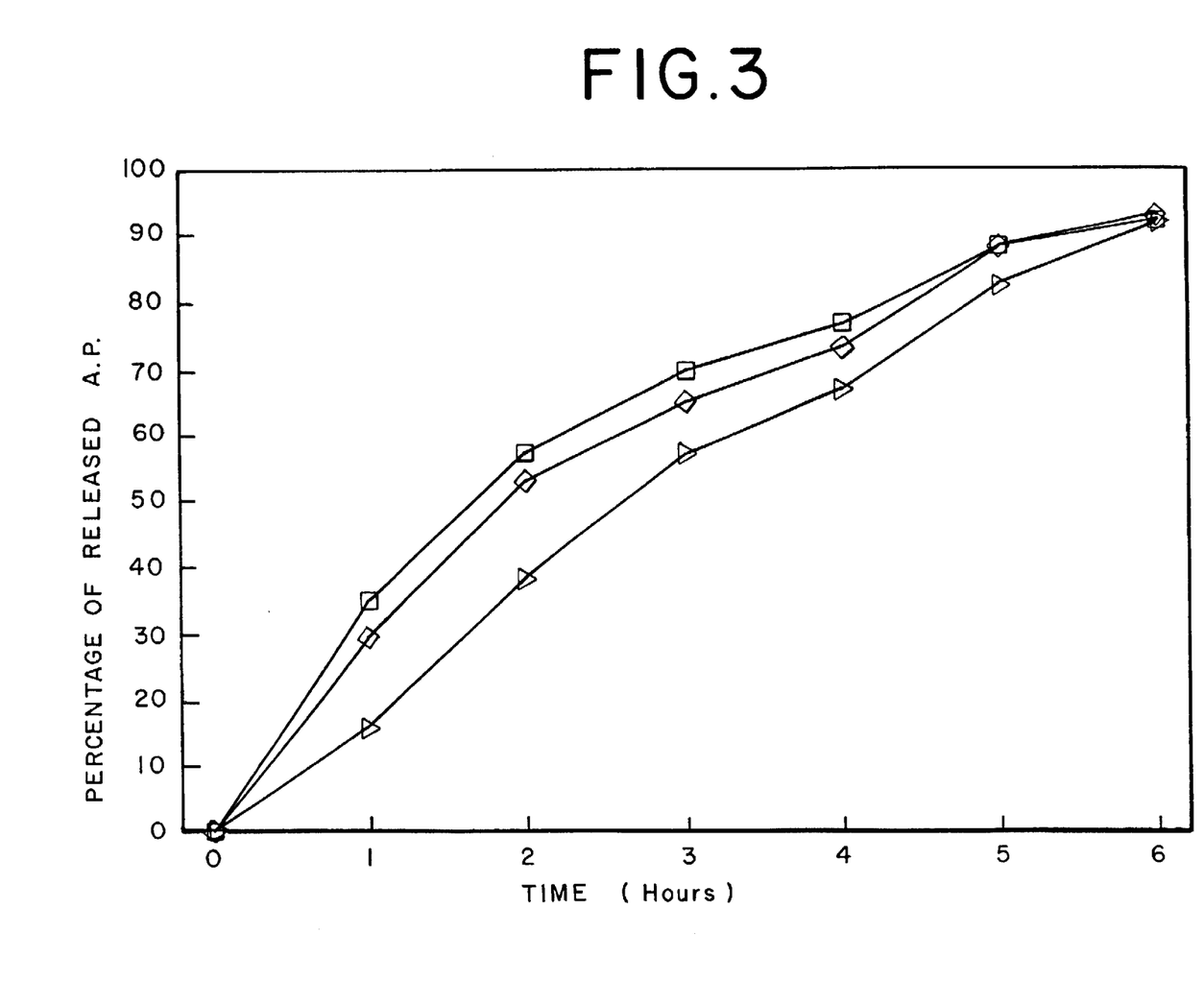

The corresponding release profile are reported in FIG. 3.

It has been unexpectedly found that the right coupling between a tablet or a granule realized as described and the filming matrix based on Eudragit® can substantially reduce the GHBNa in vitro release.

In this way, we pass from 100% active principle release with the presently available formulations on the market, to formulations having an active principle release reduced to about ¼ after the first hour and reaching a 90% release of the same not before 8 hours.

It is therefore possible to limit GHBNa administrations at not more than 2 daily administrations, compared to the nowadays required 3–4 daily administrations, with substantial advantages for the adhesion to pharmacological posology and a proportional reduction of the side effects: as a matter of fact, it is guaranteed, with this kind of release a reduction of the side effects: it is in fact guaranteed with this kind of release of the active principle a lower, but more prolonged concentration of GHBNa in plasma, for the same values of administered dose.

CLINICAL TRIALS

The two formulations reported respectively in example 1 and 2 are experimented "in vivo" by administering them at the dose of a single daily tablet to 12 voluntary healthy subjects previously divided into 2 groups.

Both formulations had 8.2% by weight of filming matrix.

The formulation indicated as RET-4 corresponds to the pharmaceutical composition of Example 2, whereas the one indicated as RET-5 corresponds to the pharmaceutical composition of Example 1.

Hematic GHB was carried out on plasma by means of gas chromatography.

The hematic samples are taken on the voluntary subjects at the following times:
first sample: after 30–45 minutes from the administration
second sample: after 60–75 minutes from the administration
third sample: after 120 from the administration
fourth sample: after 240 minutes from the administration
fifth sample: after 360 from the administration
sixth sample: after 480 minutes from the administration
seventh sample: after 720 minutes from the administration The data obtained are reported in table 4 and 5.

TABLE 4

| | Formulation RET-4 mcg/ml | | | | | | | |
|---|---|---|---|---|---|---|---|---|
| Time/ | Subjects | | | | | | | |
| (min) | A | B | C | D | E | F | Average | SD |
| 30 | 1.0 | 1.1 | — | — | — | — | 1.1 | — |
| 45 | — | — | 5.8 | 4.9 | 3.9 | 4.5 | 4.8 | 0.8 |
| 60 | 4.8 | 5.1 | — | — | — | — | 4.95 | — |
| 75 | — | — | 6.7 | 6.2 | 5.3 | 5.6 | 5.95 | 0.6 |
| 120 | 7.3 | 6.2 | 7.8 | 6.8 | 6.3 | 6.4 | 6.8 | 0.6 |
| 240 | 5.7 | 5.0 | 3.5 | 4.2 | 6.0 | 2.5 | 4.5 | 1.3 |
| 360 | 2.4 | 2.3 | 2.5 | 2.1 | 2.7 | 2.0 | 2.3 | 0.3 |
| 480 | 1.1 | 1.4 | 2.0 | 0.9 | 1.3 | 1.0 | 1.3 | 0.4 |
| 720 | 0.8 | 0.7 | 0.5 | 0.7 | 0.7 | 0.8 | 0.7 | 0.1 |

TABLE 5

| | Formulation RET-5 mcg/ml | | | | | | | |
|---|---|---|---|---|---|---|---|---|
| Time/ | Subjects | | | | | | | |
| (min) | G | H | L | M | N | P | Average | S.D. |
| 30 | 7.5 | 4.8 | 6.0 | 4.8 | 5.2 | 4.8 | 5.5 | 1.1 |
| 60 | 12.8 | 13.7 | 12.6 | 11.7 | 12.2 | 9.9 | 12.1 | 1.3 |
| 120 | 9.1 | 8.8 | 7.3 | 7.7 | 6.9 | 8.0 | 8.0 | 0.8 |
| 240 | 2.6 | 2.0 | 2.4 | 2.0 | 2.0 | 3.1 | 2.3 | 0.4 |
| 360 | 1.0 | 0.7 | 1.0 | 0.7 | 1.1 | 1.8 | 1.0 | 0.4 |
| 480 | 0.3 | 0 | — | 0.2 | 0 | 0.4 | 0.2 | 0.2 |
| 720 | 0 | 0 | 0 | 0 | 0 | 0 | 0 | 0 |

Figure 4:
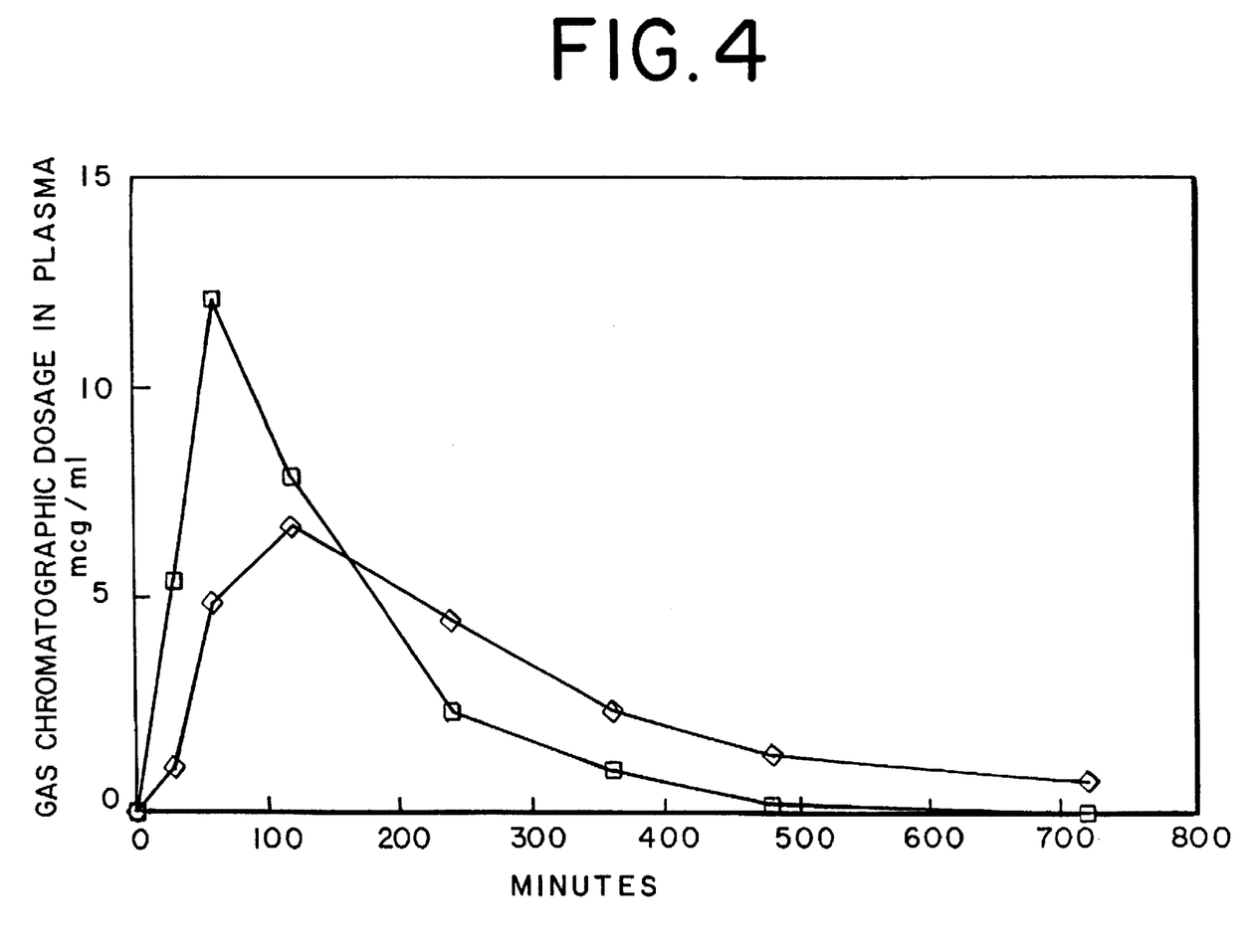

In FIG. 4 the graphic diagram is reported in mcg/ml vs. minutes of the hematic levels, obtained with the above mentioned controlled release pharmaceutical compositions 1 and 2.

Figure 5:
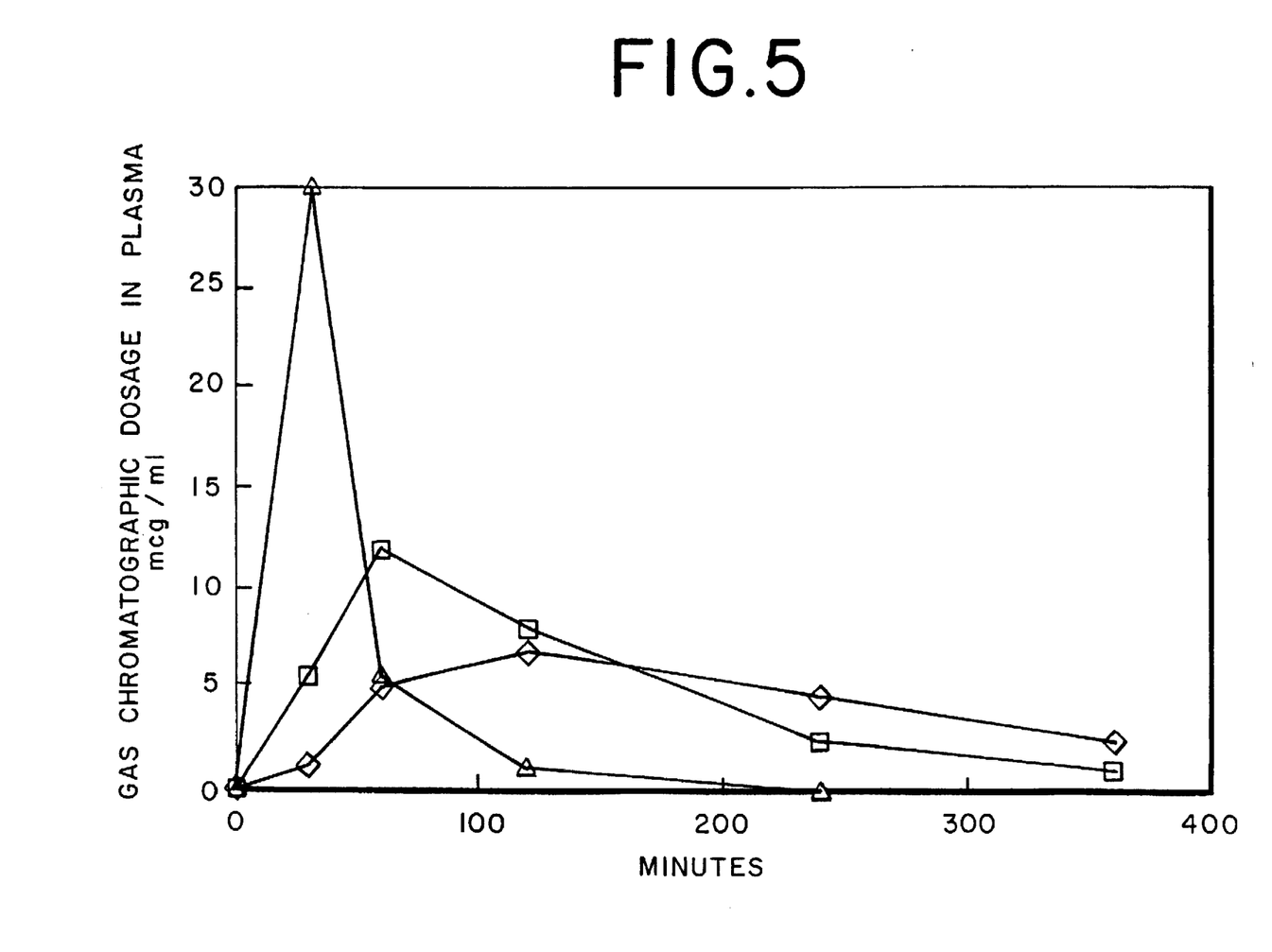

In FIG. 5 the graphic diagram of the hematic levels of these compositions are compared with the corresponding one of Alcover® syrup, containing GHB as active ingredient in a not controlled release form.

We claim:

1. Controlled release pharmaceutical compositions administrable by the oral route, containing as the active principle at least one salt of the gamma-hydroxy-butyric acid having a pharmaceutically acceptable cation, consisting of:
   (a) a nucleus in the form of granules or tablets comprising said active principle dispersed in from 2.5 to 75% by weight based on the active principle weight of a cellulosic matrix consisting of a mixture of ethylcellulose and hydroxy-propyl-methyl-cellulose having a viscosity of 100,000 cps, and wherein the weight ratio between ethylcellulose and hydroxy-propyl-methyl-cellulose is comprised between 5 and 50%,
   (b) from 2.5 to 20% by weight based on the total nucleus weight of a filming coating consisting of a mixture of two water insoluble acrylic and methacrylic acid ester copolymers in a weight ratio comprised between 0.5:10 and 10:0.5, these copolymers containing the following repeating units:

wherein $R_1$ is H or methyl, $R_2$ is methyl or ethyl, $R_3$ is methyl, $R_4$ is $R_4$ is $-CH_2CH_2^{(+)}N(CH_3)_3Cl^{(-)}$, the first copolymer containing 5% by weight of the second repeating unit, and the second copolymer containing 10% by weight of the second repeating unit.

2. A process for the preparation of controlled release pharmaceutical compositions, administrable by oral route, containing as active principle at least one salt of gamma-hydroxy-butyric acid with a pharmaceutically acceptable cation, consisting of:
   (a) a nucleus in the form of granules or tablets comprising said active principle dispersed in from 2.5 to 75% by weight based on the active principle weight of a cellulosic matrix consisting of a mixture of ethylcellulose and hydroxy-propyl-methyl-cellulose having a viscosity of 100,000 cps, and wherein the weight ratio between ethylcellulose and hydroxy-propyl-methyl-cellulose is comprised between 5 and 50%,
   (b) from 2.5 to 20% by weight based on the total nucleus weight of a filming coating consisting of a mixture of two water insoluble acrylic and methacrylic acid ester copolymers in a weight ratio comprised between 0.5:10 and 10:0.5, these copolymers containing the following repeating units:

wherein $R_1$ is H or methyl, $R_2$ is methyl or ethyl, $R_3$ is methyl, $R_4$ is $-CH_2CH_2^{(+)}N(CH_3)_3^{(-)}Cl$,
the first copolymer containing 5% by weight of the second repeating unit, and the second copolymer containing 10% by weight of the second repeating unit said process comprising the following steps:
   (i) the active principle is dry mixed with hydroxy-propyl-methyl-cellulose and optionally with a portion of ethylcellulose and the remaining part of ethylcellulose is added in the form of a solution, suspension or dispersion in an alcoholic solvent, the mixture is granulated under wet condition, then the obtained granulate is dried thus obtaining the controlled release pharmaceutical composition, in the form of granules wherein the nucleus (a) contains the active principle dispersed in the cellulosic matrix;
   (ii) the granulate from step (i), optionally added with excipients selected from antisticking agents, lubricating agents and moisture protecting agents or their mixture, is subjected to compression in order to obtain the corresponding tablets;
   (iii) the tablets from the step (ii) are submitted to a filming coating by spraying a dispersion containing: from 2 to 10% by weight of a mixture of said acrylic or methacrylic acid ester copolymers, containing the above mentioned repeating units, wherein $R_1$, $R_2$, $R_3$, $R_4$ have the above defined meanings, in said mixture in weight ratio comprised between 0.5:10 and 10:0.5;

a mixture of one or more alcoholic solvents and/or one or more ketonic solvents in order to have on said nucleus a polymer coating ranging from 2.5 to 20% by weight based on the total nucleus weight.

3. A process for the preparation of controlled release pharmaceutical compositions, administrable by oral route, containing as active principle at least one salt of gamma-hydroxy-butyric acid with a pharmaceutically acceptable cation, consisting of:

(a) a nucleus in the form of granules or tablets comprising said active principle dispersed in from 2.5 to 75% by weight based on the active principle dispersed in from 2.5 to 75% by weight based on the active principle weight of a cellulosic matrix consisting of a mixture of ethylcellulose and hydroxy-propyl-methyl-cellulose having a viscosity of 100,000 cps, and wherein the weight ratio between ethylcellulose and hydroxy-propyl-methyl-cellulose is comprised between 5 and 50%, (b) from 2.5 to 20% by weight based on the total nucleus weight of a filming coating consisting of a mixture of two water insoluble acrylic and methacrylic acid ester copolymers in a weight ratio comprised between 0.5:10 and 10:0.5, these copolymers containing the following repeating units:

wherein $R_1$ is H or methyl, $R_2$ is methyl or ethyl, $R_3$ is methyl, $R_4$ is $-CH_2Ch_2^{(+)}N(CH_3)_3Cl^{(-)}$, the first copolymer containing 5% by weight of the second repeating unit, and the second copolymer containing 10% by weight of the second repeating unit said process comprising the following steps:

(i) the active principle is dry mixed with hydroxy-propyl-methyl-cellulose and optionally with a portion of ethylcellulose and the remaining part of ethylcellulose is added in the form of a solution, suspension or dispersion in an alcoholic solvent, the mixture is granulated under wet condition, then the obtained granulate is dried thus obtaining the controlled release pharmaceutical composition, in the form of granules wherein the nucleus (a) contains the active principle dispersed in the cellulosic matrix;

(ii) the granules from step (i) are submitted to a filming coating by spraying a dispersion containing:

from 2 to 10% by weight of a mixture of said acrylic or methacrylic acid ester copolymers, containing the above mentioned repeating units, wherein $R_1$, $R_2$, $R_3$, $R_4$ have the above defined meanings, in said mixture in weight ratio comprised between 0.5:10 and 10:0.5;

a mixture of one or more alcoholic solvents and/or one or more ketonic solvents in order to have on said nucleus a polymer coating ranging from 2.5 to 20% by weight based on the total nucleus weight.

4. The pharmaceutical compositions according to claim 1, wherein the hydroxy-propyl-methyl-cellulose and at least 50% of the total granulometry is comprised between 20 and 200 microns.

5. The pharmaceutical compositions as claimed in claim 1 for the treatment of alcoholism, opium like substances addiction, heroin addiction, food and nicotine addiction and for the treatment of depressive and anxious states.

6. The pharmaceutical compositions as claimed in claim 1, wherein the salts of gamma-hydroxy-butyric acid are selected from the group consisting of sodium, lithium, potassium, magnesium and calcium salts.

7. The pharmaceutical compositions as claimed in claim 1, wherein ethylcellulose shows a viscosity comprised between 5 and 200 cps.

8. The pharmaceutical compositions as claimed in claim 7, wherein ethylcellulose shows an average viscosity of 22 cps.

9. The pharmaceutical compositions as claimed in claim 1, wherein nucleus (a) contains other excipients selected from antisticking agents, agents able to give the correct degree of lubrication, moisture proof agents or mixtures thereof.

10. The pharmaceutical compositions as claimed in claim 9, wherein talc is used as antisticking agent, magnesium stearate is the lubricating agent and colloidal silica is the moisture proof agent.

11. The pharmaceutical compositions as claimed in claim 1, wherein the film protection consists of polymer selected from hydroxy-propyl-cellulose, hydroxy-propyl-methylcellulose, polyvinyl-pyrrolidone, polyoxyethylen glycol.

12. The process as claimed in claim 2, wherein the alcoholic solvent used in step i) is ethanol and the solvent used for the dispersion of the step iii) is a mixture of isopropanol and acetone in a volumetric ratio 1:1.

* * * * *